(12) United States Patent
Farazi et al.

(10) Patent No.: US 8,401,627 B1
(45) Date of Patent: Mar. 19, 2013

(54) METHODS AND SYSTEMS FOR MONITORING HEART INSTABILITIES

(75) Inventors: Taraneh Ghaffari Farazi, San Jose, CA (US); Fujian Qu, Sunnyvale, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1288 days.

(21) Appl. No.: 11/848,631

(22) Filed: Aug. 31, 2007

(51) Int. Cl.
*A61N 1/362* (2006.01)

(52) U.S. Cl. ........ 600/515; 600/508; 600/509; 600/516; 600/517; 607/9; 607/14; 607/25; 607/26

(58) Field of Classification Search ............... 600/9, 14, 600/25, 26, 70, 74, 508–509, 515–517; 607/508–509, 515–517, 68, 73, 9, 14, 25, 607/26, 70, 74
See application file for complete search history.

(56) References Cited

U.S. PATENT DOCUMENTS

| | | | |
|---|---|---|---|
| 5,555,888 A * | 9/1996 | Brewer et al. ................. | 600/515 |
| 5,913,877 A | 6/1999 | Kroll | |
| 6,341,235 B1 | 1/2002 | Mower | |
| 6,343,232 B1 | 1/2002 | Mower | |
| 6,484,056 B2 | 11/2002 | Fisher | |
| 6,823,213 B1 * | 11/2004 | Norris et al. ...................... | 607/9 |
| 2005/0004608 A1 | 1/2005 | Bullinga | |
| 2005/0049516 A1 * | 3/2005 | Ideker ........................... | 600/516 |

OTHER PUBLICATIONS

Li, Mingyi et al., "Controlling Alternans in Cardiac Cells," Ann Biomed Eng., Jun. 2004;32(6): 784-792.
Pastore, Joseph et al., "Mechanism Linking T-Wave Alternans to the Genesis of Cardiac Fibrillation," Circulation 1999;99;1285-1294.
Shimizu, Wataru et al., "Cellular and Ionic Basis for T-Wave Alternans Under Long-QT Conditions," Circulation 1999;99;1499-1507.

\* cited by examiner

*Primary Examiner* — Carl H Layno
*Assistant Examiner* — Jennifer Ghand
(74) *Attorney, Agent, or Firm* — Steven M. Mitchell

(57) ABSTRACT

Systems and method for assessing a patient's myocardial electrical stability by pacing a patient's heart using a pacing sequence that includes at least two different types of pacing pulses. The pacing rate used is preferably only slightly above the patient's intrinsic heart rate. A degree of alternans, in a signal (e.g., IEGM or ECG) that is indicative of cardiac activity in response to the pacing sequence, is determined. The degree of alternans can be determined by comparing portions of the signal that are indicative of cardiac activity in response to the first type of pacing pulses to portions of the signal that are indicative of cardiac activity in response to the second type of pacing pulses. The patient's myocardial electrical stability is assessed based on the determined degree of alternans.

23 Claims, 11 Drawing Sheets

Monophasic Pacing Pulse

Biphasic Pacing Pulse

Pacing Pulses

Monophasic (M) Pulse

Biphasic (B) Pulse

Heart Failure

METHODS AND SYSTEMS FOR MONITORING HEART INSTABILITIES

FIELD OF THE INVENTION

Embodiments of the present invention generally relate to methods and systems that are capable of monitoring heart instabilities.

BACKGROUND

Although a variety of methods have been developed, prediction of tachyarrhythmias and sudden cardiac death remains a difficult and often imperfect procedure. Recently, analysis of microvolt level T-wave alternans (TWA) has been introduced as a new approach to evaluate arrhythmia risk. TWA, an ECG phenomenon, is a manifestation of the intrinsic heart instabilities. The underling causes of tachyarrhythmia and sudden cardiac death are believed to be the alternans in electrical wave propagation and action potential repolarization.

The following articles, which are incorporated herein by reference, provide additional details about T-wave alternans analysis: Pastore et al. "Mechanism linking T-wave alternans to the genesis of cardiac fibrillation." Circulation. 1999 Mar. 16; 99(10):1385-94; and Shimizu et al. "Cellular and ionic basis for T-wave alternans under long-QT conditions." Circulation. 1999 Mar. 23; 99(11):1499-507.

The degree of T-wave alterations has been found to be tightly associated with heart diseases such as ischemia, myocardial infarction, heart failure, etc. However, it has generally been believed that a substantially elevated heart rate is required in order to detect TWA, which would be unpleasant and potentially arrhythmogenic procedure for certain patient populations. It would be beneficial if TWA, or more generally, electrical alternans, could be detected at normal heart rates.

SUMMARY

Embodiments of the present invention relate to systems and method for assessing a patient's myocardial electrical stability. In accordance with specific embodiments, a patient's heart is paced using a pacing sequence that includes at least two different types of pacing pulses. The pacing rate used is preferably only slightly above the patient's intrinsic heart rate to ensure capture. A degree of alternans, in a signal (e.g., an IEGM or ECG) that is indicative of cardiac activity in response to the pacing sequence, is determined. The degree of alternans can be determined by comparing portions of the signal that are indicative of cardiac activity in response to a first type of pacing pulses to portions of the signal that are indicative of cardiac activity in response to a second type of pacing pulses. The patient's myocardial electrical stability is assessed based on the determined degree of alternans.

In specific embodiments, the pacing sequence includes both monophasic and biphasic pacing pulses. For example, the pacing sequence can include alternating monophasic and biphasic pacing pulses. Alternatively, the pacing sequence can include a plurality of monophasic pacing pulses followed by a plurality of biphasic pacing pulses, which may or may not be repeated. In other embodiments, the pacing sequence can include different types of biphasic pacing pulses. Alternatively, the pacing sequence can include different types of monophasic pacing pulses.

In accordance with specific embodiments, a patient's risk of a tachyarrhythmia or sudden cardiac death (SCD) can be assessed based on a determined degree of alternans. Also, an alert and/or response can be triggered, e.g., if there is an assessment that the patient is at risk of a tachyarrhythmia.

Techniques of the present invention can be repeated over time, to monitor changes in a cardiac disease based on changes in determined degrees of alternans. The cardiac disease that is being monitored can be, e.g., ischemia and/or heart failure. A reduction in the degree of alternans can be interpreted as being indicative of an improvement in the cardiac disease, and an increase in the degree of alternans can be interpreted as being indicative of a worsening of the cardiac disease.

This summary is not intended to be a complete description of the invention. Other features and advantages of the invention will appear from the following description in which the preferred embodiments have been set forth in detail, in conjunction with the accompanying drawings and claims.

BRIEF DESCRIPTION OF THE DRAWINGS

FIG. 6A is essentially the same of FIG. 5C.

DETAILED DESCRIPTION

The following detailed description of the present invention refers to the accompanying drawings that illustrate exemplary embodiments consistent with this invention. Other embodiments are possible, and modifications may be made to the embodiments within the spirit and scope of the present invention. Therefore, the following detailed description is not meant to limit the invention. Rather, the scope of the invention is defined by the appended claims.

It would be apparent to one of skill in the art that the present invention, as described below, may be implemented in many different embodiments of hardware, software, firmware, and/or the entities illustrated in the figures. Any actual software and/or hardware described herein is not limiting of the present invention. Thus, the operation and behavior of the present invention will be described with the understanding that modifications and variations of the embodiments are possible, given the level of detail presented herein.

Embodiments of the present invention relate to methods and systems for assessing heart instability at regular heart rates via programmed stimulation. These embodiments can be used as a risk indicator of tachyarrhythmia and/or sudden cardiac death, and/or as a diagnostic tool to detect and track heart diseases such as ischemia and/or heart failure.

Figure 1:
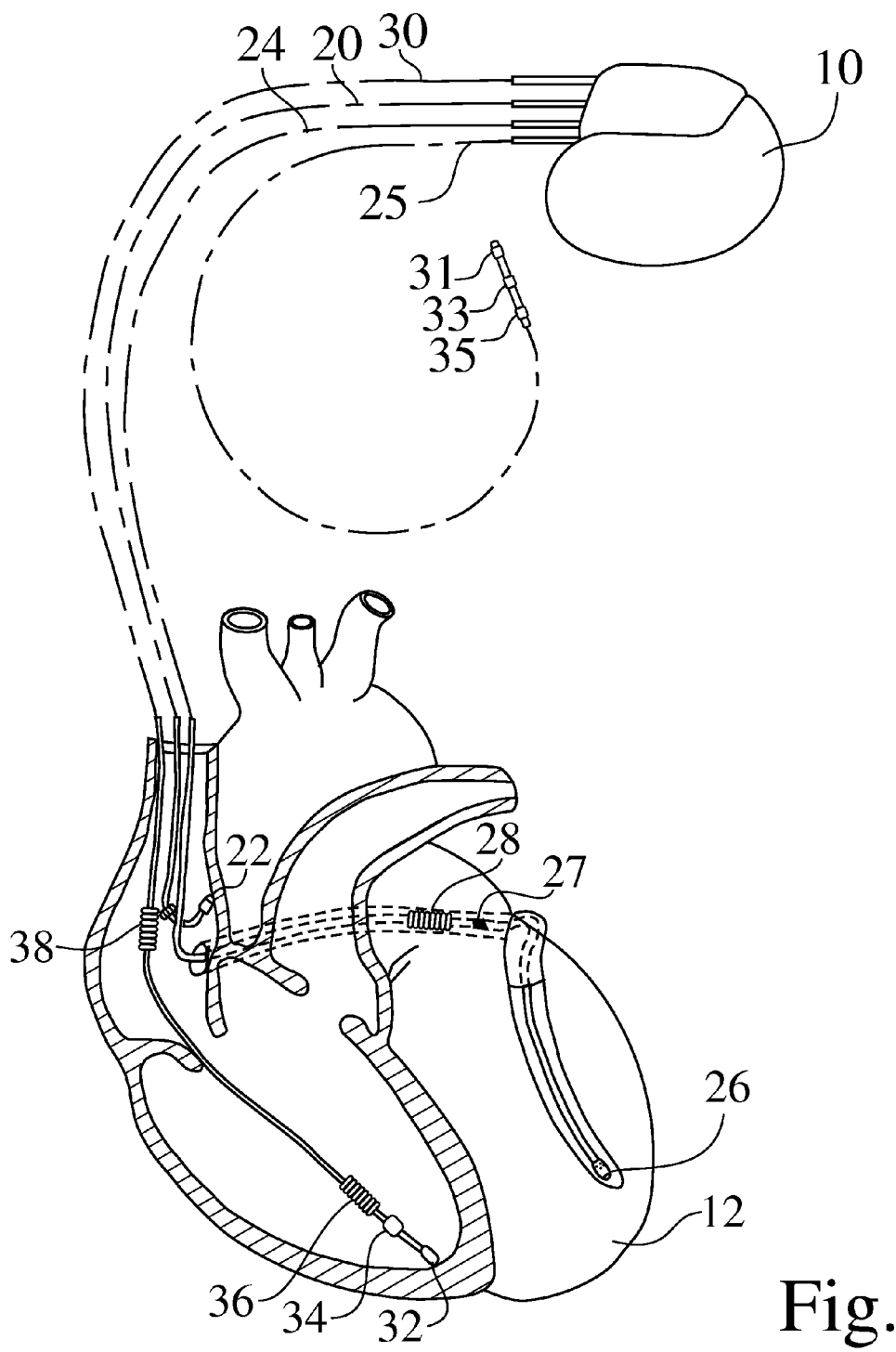
FIG. 1 is a simplified diagram illustrating an exemplary ICD in electrical communication with a patient's heart by means of three leads suitable for delivering multi-chamber stimulation and pacing therapy, and a fourth lead suitable for delivering vagal stimulation.
Figure 2:
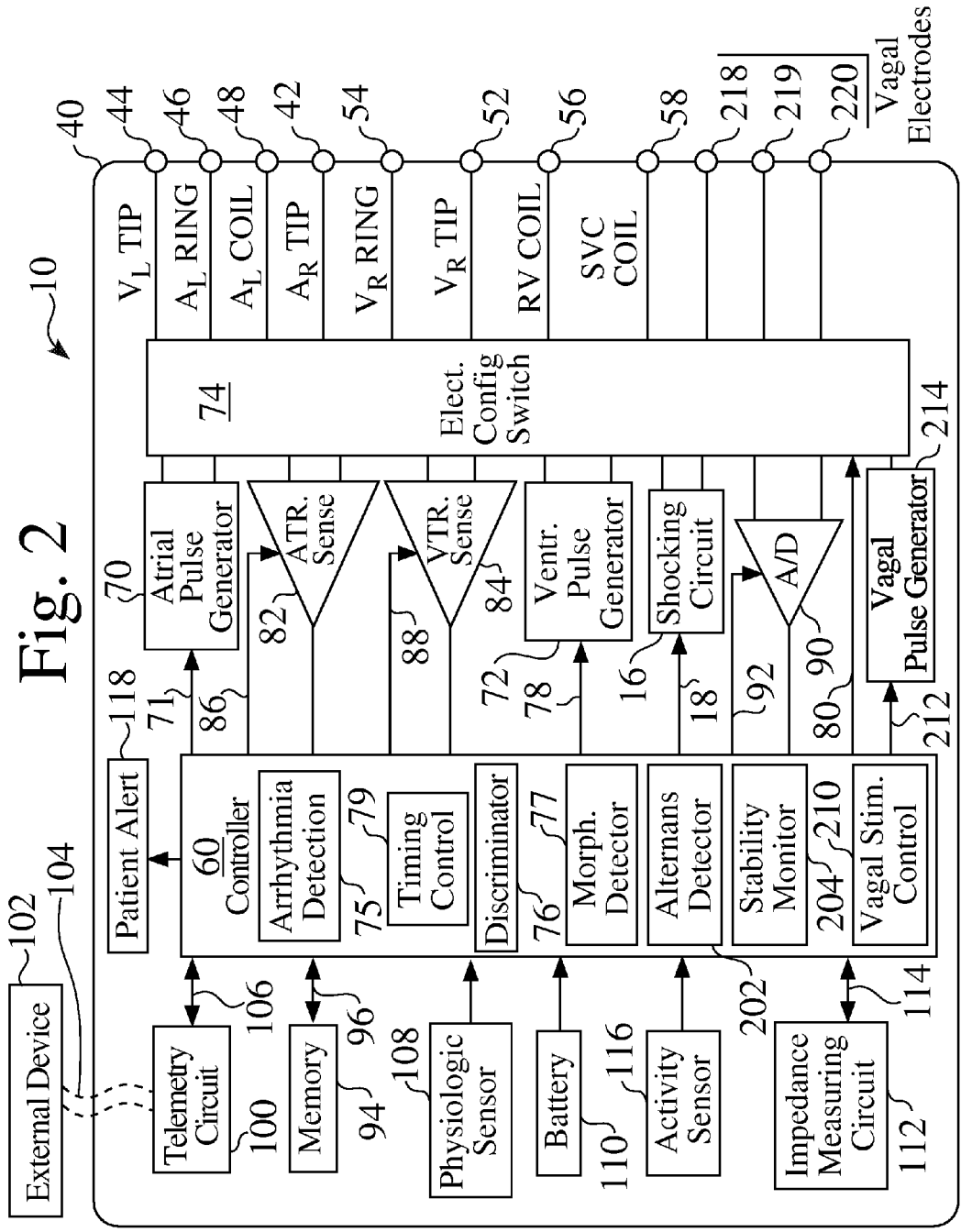
FIG. 2 is a functional block diagram of an exemplary ICD that can provide cardioversion, defibrillation, and pacing stimulation in four chambers of a heart, and monitor myocardial electrical stability, in accordance with embodiments of the present invention.

Before describing the invention in detail, it is helpful to describe an example environment in which embodiments of the present invention may be implemented. Embodiments of the present invention are particularly useful in the environment of an implantable cardiac device that can monitor electrical activity of a heart and deliver appropriate electrical therapy, for example, pacing pulses, cardioverting and defibrillator pulses, and drug therapy, as required. Implantable cardiac devices include, for example, pacemakers, cardioverters, defibrillators, implantable cardioverter defibrillators, and the like. The term "implantable cardiac device" or simply "ICD" is used herein to refer to any implantable cardiac device. FIGS. 1 and 2 illustrate such an environment in which embodiments of the present invention can be used.

Exemplary ICD

Referring first to FIG. 1, an exemplary ICD 10 is shown in electrical communication with a patient's heart 12 by way of three leads, 20, 24 and 30, suitable for delivering multi-chamber stimulation and pacing therapy. To sense atrial cardiac signals and to provide right atrial chamber stimulation therapy, ICD 10 is coupled to implantable right atrial lead 20 having at least an atrial tip electrode 22, which typically is implanted in the patient's right atrial appendage.

To sense left atrial and ventricular cardiac signals and to provide left-chamber pacing therapy, ICD 10 is coupled to "coronary sinus" lead 24 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

ICD 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, right ventricular lead 30 is transvenously inserted into heart 12 so as to place the right ventricular tip electrode 32 in the right ventricular apex so that RV coil electrode 36 will be positioned in the right ventricle and SVC coil electrode 38 will be positioned in the SVC. Accordingly, right ventricular lead 30 is capable of receiving cardiac signals and delivering stimulation in the form of pacing and shock therapy to the right ventricle. Alternative and additional leads and electrodes can be used to sense, pace and shock the patient's heart, as is well known in the art.

In FIG. 1, ICD 10 is also shown as being in electrical communication with the patient's heart 12 by way of a vagal stimulation lead 25, having, e.g., three vagal stimulation electrodes 31, 33, and 35 capable of delivering stimulation bursts to the patient's vagus nerve. Alternatively, vagal stimulation electrodes 31, 33, and 35 can be positioned in the epicardial fat pad near the sinoatrial (SA) node. Based on the description herein, one skilled in the relevant art(s) will understand that the invention can be implemented by positioning vagal stimulation electrodes 31, 33, and 35 in alternate locations, such as in proximity to the cervical vagus, or implanted near or inside the SVC, the inferior vena cava (IVC), or the coronary sinus (CS), where they are also capable of delivering stimulation bursts to the patient's vagus nerve.

FIG. 2 shows a simplified block diagram of ICD 10, which is capable of treating both fast and slow arrhythmias with stimulation therapy, including cardioversion, defibrillation, and pacing stimulation. While a particular multi-chamber device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of ICD 10, shown schematically in FIG. 2, is often referred to as the "can," "case" or "case electrode" and may be programmably selected to act as the return electrode for all "unipolar" modes. Housing 40 may further be used as a return electrode alone or in combination with one or more of coil electrodes, 28, 36, and 38 for shocking purposes. Housing 40 further includes a connector (not shown) having a plurality of terminals, 42, 44, 46, 48, 52, 54, 56, 58, 218, 219 and 220 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to atrial tip electrode 22.

To achieve left chamber sensing, pacing and shocking, the connector includes at least a left ventricular tip terminal (VL TIP) 44, a left atrial ring terminal (AL RING) 46, and a left atrial shocking terminal (AL COIL) 48, which are adapted for connection to left ventricular ring electrode 26, left atrial tip electrode 27, and left atrial coil electrode 28, respectively.

To support right chamber sensing, pacing, and shocking the connector also includes a right ventricular tip terminal (VR TIP) 52, a right ventricular ring terminal (VR RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

The connector is also shown as including vagal lead terminals (VAGAL ELECTRODES) 218, 219, and 220, which are configured for connection to vagal stimulation electrodes 31, 33, and 35, respectively, to support the delivery of vagal stimulation bursts.

At the core of ICD 10 is a programmable microcontroller 60, which controls the various modes of stimulation therapy. As is well known in the art, microcontroller 60 typically includes one or more microprocessor, or equivalent control circuitry, designed specifically for controlling the delivery of stimulation therapy and can further include RAM or ROM memory, logic and timing circuitry, state machine circuitry, and I/O circuitry. Typically, microcontroller 60 includes the ability to process or monitor input signals (data) as controlled by a program code stored in a designated block of memory. The details of the design of microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et. al.) and the state-machines of U.S. Pat. Nos. 4,712,555 (Sholder) and 4,944,298 (Sholder). For a more detailed description of the various timing intervals used within the ICD's and their interrelationship, see U.S. Pat. No. 4,788,980 (Mann et. al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, atrial and ventricular pulse generators 70 and 72 may include dedicated, independent pulse generators, multiplexed pulse generators, or shared pulse generators. Pulse generators 70 and 72 are controlled by microcontroller 60 via appropriate control signals 71 and 78, respectively, to trigger or inhibit the stimulation pulses.

Also shown in FIG. 2, is a vagal pulse generator 214 that is controlled by vagal stimulation control 210 (within microcontroller 60) via a control signal 212, to trigger or inhibit the delivery of vagal stimulation pulses.

Microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

Switch 74 includes a plurality of switches for connecting the desired electrodes to the appropriate I/O circuits, thereby providing complete electrode programmability. Accordingly, switch 74, in response to a control signal 80 from microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to right atrial lead 20, coronary sinus lead 24, and right ventricular lead 30, through switch 74 for detecting the presence of cardiac activity in each of the four chambers of the heart. Accordingly, the atrial (ATR. SENSE) and ventricular (VTR. SENSE) sensing circuits 82 and 84 may include dedicated sense amplifiers, multiplexed amplifiers, or shared amplifiers. Switch 74 determines the "sensing polarity" of the cardiac signal by selectively closing the appropriate switches, as is also known in the art. In this way, a clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables ICD 10 to deal effectively with the difficult problem of sensing the low amplitude signal characteristics of atrial or ventricular fibrillation. Such sensing circuits, 82 and 84, can be used to determine cardiac performance values used in the present invention.

The outputs of atrial and ventricular sensing circuits 82 and 84 are connected to microcontroller 60 which, in turn, are able to trigger or inhibit atrial and ventricular pulse generators, 70 and 72, respectively, in a demand fashion in response to the absence or presence of cardiac activity, in the appropriate chambers of the heart. Sensing circuits 82 and 84, in turn, receive control signals over signal lines 86 and 88 from microcontroller 60 for purposes of measuring cardiac performance at appropriate times, and for controlling the gain, threshold, polarization charge removal circuitry (not shown), and timing of any blocking circuitry (not shown) coupled to the inputs of sensing circuits 82 and 86.

For arrhythmia detection, ICD 10 utilizes the atrial and ventricular sensing circuits 82 and 84 to sense cardiac signals to determine whether a rhythm is physiologic or pathologic. The timing intervals between sensed events (e.g., P-waves, R-waves, and depolarization signals associated with fibrillation are then classified by microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Microcontroller 60 can utilize arrhythmia detector 75, and/or morphology detector 77 to recognize and classify arrhythmia so that appropriate therapy can be delivered. The morphology detector 77 may also be used to detect signal morphologies that are useful for detecting electrical alternans, in accordance with embodiments of the present invention described below. The arrhythmia detector 75, discriminator 76, and morphology detector 77 can be implemented within the microcontroller 60, as shown in FIG. 2. Thus, these elements can be implemented by software, firmware, or combinations thereof. It is also possible that all, or portions, of these detectors can be implemented using hardware.

Cardiac signals are also applied to the inputs of an analog-to-digital (ND) data acquisition system 90. Data acquisition system 90 is configured to acquire intracardiac electrogram signals, convert the raw analog data into a digital signal, and store the digital signals for later processing and/or telemetric transmission to an external device 102. Data acquisition system 90 is coupled to right atrial lead 20, coronary sinus lead 24, and right ventricular lead 30 through switch 74 to sample cardiac signals across any pair of desired electrodes.

Data acquisition system 90 can be coupled to microcontroller 60, or other detection circuitry, for detecting an evoked response from heart 12 in response to an applied stimulus, thereby aiding in the detection of "capture." Capture occurs when an electrical stimulus applied to the heart is of sufficient energy to depolarize the cardiac tissue, thereby causing the heart muscle to contract. Microcontroller 60 detects a depolarization signal during a window following a stimulation pulse, the presence of which indicates that capture has occurred. Microcontroller 60 enables capture detection by triggering ventricular pulse generator 72 to generate a stimulation pulse, starting a capture detection window using timing control circuitry 79 within microcontroller 60, and enabling data acquisition system 90 via a control signal 92 to sample the cardiac signal that falls in the capture detection window and, based on the amplitude, determines if capture has occurred. Additionally, microcontroller 60 can detect cardiac events, such as premature contractions of ventricles, and the like.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

Microcontroller 60 is further coupled to a memory 94 by a suitable data/address bus 96, wherein the programmable operating parameters used by microcontroller 60 are stored and modified, as required, in order to customize the operation of ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to heart 12 within each respective tier of therapy.

The operating parameters of ICD 10 may be non-invasively programmed into memory 94 through telemetry circuit 100 in telemetric communication with external device 102, such as a programmer, transtelephonic transceiver, or a diagnostic system analyzer. Telemetry circuit 100 is activated by microcontroller 60 by a control signal 106. Telemetry circuit 100 advantageously allows intracardiac electrograms and status information relating to the operation of ICD 10 (as contained in microcontroller 60 or memory 94) to be sent to external device 102 through established communication link 104.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

ICD 10 further includes a physiologic sensor 108 that can be used to detect changes in cardiac performance or changes in the physiological condition of the heart. Accordingly, microcontroller 60 can respond by adjusting the various pacing parameters (such as rate, AV Delay, RV-LV Delay, V-V Delay, etc.). Microcontroller 60 controls adjustments of pacing parameters by, for example, controlling the stimulation pulses generated by the atrial and ventricular pulse generators 70 and 72. While shown as being included within ICD 10, it is to be understood that physiologic sensor 108 may also be external to ICD 10, yet still be implanted within or carried by the patient. More specifically, sensor 108 can be located inside ICD 10, on the surface of ICD 10, in a header of ICD 10, or on a lead (which can be placed inside or outside the bloodstream).

Also shown in FIG. 2 is an activity sensor 116. The activity sensor 116 (e.g., an accelerometer) can be used to determine the activity of the patient. Such information can be used for rate responsive pacing, or, in accordance with embodiments of the present invention, to determine whether the patient is sufficiently at rest such that certain baseline measurements can be obtained. If the sensor 116 is a multi-dimensional accelerometer, then posture information can also be extracted. The following patents, which are incorporated herein by reference, describe exemplary activity sensors that can be used to detect activity of a patient (some also detect posture): U.S. Pat. No. 6,658,292 to Kroll et al., entitled "Detection of Patient's Position and Activity Status using 3D Accelerometer-Based Position Sensor"; U.S. Pat. No. 6,466,821 to Kroll et al., entitled "Orientation of Patient's Position Sensor using External Field"; and U.S. Pat. No. 6,625,493 to Pianca et al., entitled "AC/DC Multi-Axis Accelerometer for Determining Patient Activity and Body Position." Simple activity sensors employ a piezoelectric crystal or a cantilever beam having a film of a piezoelectric polymer adhered to a surface of the beam. These are just a few exemplary types of activity sensors 116, which are not meant to be limiting.

The ICD 10 may also include a magnet detection circuitry (not shown), coupled to microcontroller 60. It is the purpose of the magnet detection circuitry to detect when a magnet is placed over ICD 10. A clinician may use the magnet to perform various test functions of ICD 10 and/or to signal microcontroller 60 that the external programmer 102 is in place to receive or transmit data to microcontroller 60 through telemetry circuit 100.

As further shown in FIG. 2, ICD 10 can have an impedance measuring circuit 112, which is enabled by microcontroller 60 via a control signal 114. The known uses for an impedance measuring circuit 112 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to switch 74 so that any desired electrode may be used. The impedance measuring circuit 112 is not critical to the present invention and is shown only for completeness.

In the case where ICD 10 is intended to operate as a cardioverter, pacer or defibrillator, it should detect the occurrence of an arrhythmia and automatically apply an appropriate electrical therapy to the heart aimed at terminating the detected arrhythmia. To this end, microcontroller 60 further controls a shocking circuit 16 by way of a control signal 18.

The shocking circuit 16 generates shocking pulses of low (up to about 0.5 Joules), moderate (about 0.5-10 Joules), or high energy (about 11 to 40 Joules), as controlled by microcontroller 60. Such shocking pulses are applied to the patient's heart 12 through at least two shocking electrodes (e.g., selected from left atrial coil electrode 28, RV coil electrode 36, and SVC coil electrode 38). As noted above, housing 40 may act as an active electrode in combination with RV electrode 36, or as part of a split electrical vector using SVC coil electrode 38 or left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of about 5-40 Joules), delivered asynchronously (since R-waves may be too disorganized to be recognize), and pertaining exclusively to the treatment of fibrillation. Accordingly, microcontroller 60 is capable of controlling the synchronous or asynchronous delivery of the shocking pulses.

ICD 10 additionally includes a battery 110, which provides operating power to a load that includes all of the circuits shown in FIG. 2.

FIG. 2 also shows that the microcontroller 60 can include an alternans detector 202, which as described in more detail below, can detect the presence of electrical alternans. The microcontroller is also shown as including a myocardial electrical stability detector 204. The alternans detector 202 and the stability detector 204 can be implemented within the microcontroller 60, as shown in FIG. 2. Thus, the alternans detector 202 and the stability detector 204 can be implemented by software, firmware, or combinations thereof. It is also possible that all, or portions, of the alternans detector 202 and/or the stability detector 204 can be implemented using hardware. Further, it is possible that all, or portions, of the alternans detector 202 and the stability detector 204 be implemented external to the microcontroller 60. While shown as two separate blocks in FIG. 2, it is also possible that the alternans detector 202 and the stability detector 204 can be implemented as one block.

In an embodiment, the alternans detector 202 and/or stability detector 204 triggers data acquisition circuit 90 and timing control circuit 79 to record IEGM signal information when a patient is paced using patterned pacing sequences of the present invention. The alternans detector 202 can measure morphology metrics, including but not limited to T-wave metrics, such as T-wave amplitude, T-wave width, T-wave slope, T-wave area, T-wave morphology, QT interval, evoked QT interval, etc. in the IEGM signal generated by the sensing circuits of the data acquisition system 90. Morphologic metrics other than T-wave metrics can be used, such as, but not limited to, QRS amplitude and QRS width. The stability detector 204 can also trigger the implantable device 10 to respond appropriately when alternans beyond a threshold are detected, as will be explained in more detail below. Additionally, in conjunction with a telemetry circuit 100, the alternans detector 202 and/or stability detector 204 can be configured to deliver status information, relating to the patient's electrical alternans, to an external device 102 through an established communication link 104. The stability detector 204 can also trigger a patient or physician alert in response to detecting alternans beyond a threshold. For example, a patient alert 118, which produces a vibratory or auditory alert, may be triggered by the stability detector 204.

Electrical alternans have been demonstrated in many studies to be a strong predictor of mortality, independent of left ventricular ejection fraction (LVEF). It has been generally believed that a substantially elevated heart rate is a requirement for the detection of electrical alternans. However, increasing the heart rate of many patients can be unpleasant and arrhythmogenic.

Specific embodiments of the present invention relate to novel pacing schemes that can be used for detecting alternans, and more generally, for monitoring myocardial electrical stability, at heart rates only slightly above intrinsic rates. Embodiments of the present invention also relate to implantable cardiac devices such as pacemakers and/or defibrillators that deliver the novel pacing schemes of the present invention and monitor myocardial electrical stability based on a heart's response to such pacing schemes. Embodiments of the present invention also relate to non-implanted devices that are capable of controlling implanted cardiac devices, as will be understood for the description below.

Specific embodiments of the present invention use programmed stimulation to assess electrophysiological instabilities of the heart. In these techniques, a pacing sequence that includes at least two different types of pacing pulses is delivered to the heart to induce and measure the presence and degree of repolarization alternans. A number of different pacing patterns can be applied using a sequence of different types of biphasic or monophasic pacing pulses, or a combination of biphasic and monophasic pulses can be used. Unlike the conventional T-wave alternans (TWA) examination methods that need to significantly increase a patient's heart rate, embodiments of the present invention can induce alternans at heart rates that are only slightly above intrinsic rates (to ensure capture in response to pacing).

Figure 3A:
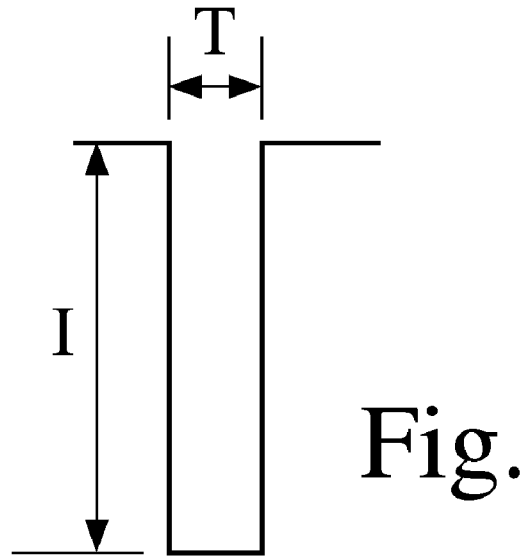
FIG. 3A is a schematic representation of an exemplary monophasic pacing pulse.
Figure 3B:
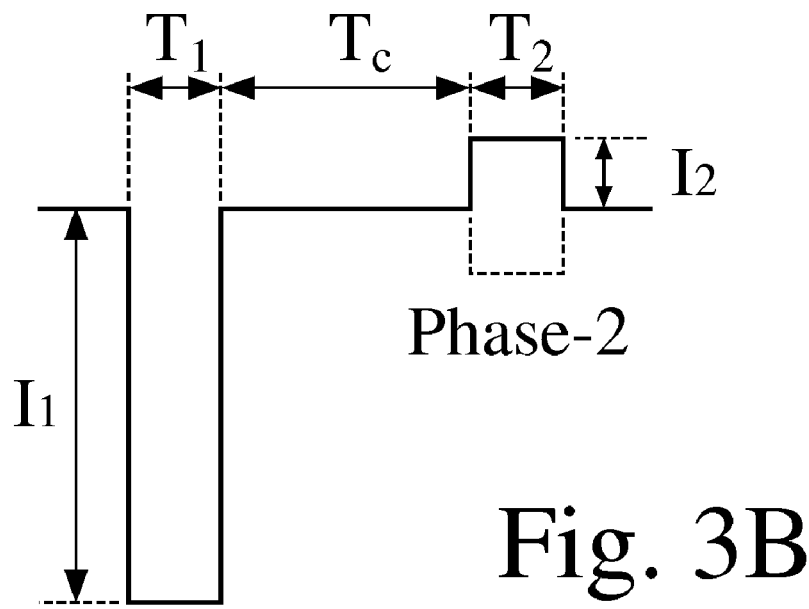
FIG. 3B is a schematic representation of an exemplary biphasic pacing pulse.

FIG. 3A illustrates an exemplary monophasic pacing pulse, which is the typical type of pacing pulse used to pace patients. As can be seen in FIG. 3A, a monophasic pacing pulse includes an amplitude (I), polarity, and a pulse duration (T). FIG. 3B illustrates an exemplary biphasic pacing pulse. As can be seen in FIG. 3B, a biphasic pacing pulse includes a first phase (phase-1), a second phase (phase-2), and a coupling interval (Tc) between the first and second phases. Each phase includes a respective amplitude (11 and 12), pulse duration (T1 and T2), and a polarity (cathode or anode). In FIG. 3B, the polarity of phase-1 pulse shown is cathode (as a regular pacing pulse). The polarity of phase-2 pulse can be the opposite of the polarity of the phase-1 pulse (i.e., anode as shown) or the same as the polarity of the phase-1 pulse (i.e., cathode as shown in phantom).

The basis of the various embodiments of the present invention were examined and verified with the computer simulations, which will be described in more detail below. However, before discussing the computer simulations, the high level flow diagram of FIG. 4 will be used to summarize various embodiments of the present invention. Such embodiments can generally be used to assess a patient's myocardial electrical stability. Such an assessment can be useful, e.g., to predict a patient's risk of a tachyarrhythmia, and/or to predict a patient's risk of sudden cardiac death (SCD).

Figure 4:
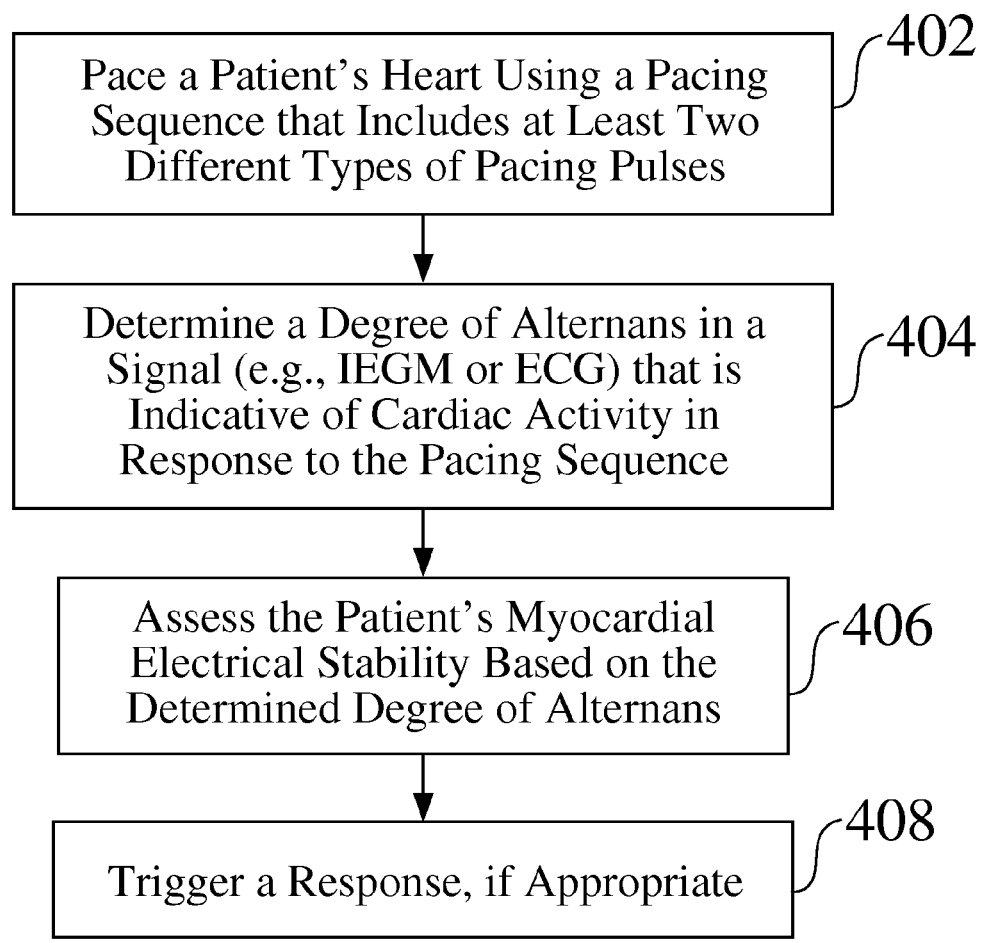
FIG. 4 is a high level flow diagram that is useful for summarizing embodiments of the present invention

The flow diagram of FIG. 4 provides an overview of the operation and novel features that can be implemented in various embodiments, e.g., of the implantable device 10 and/or external device 102. In the flow diagram, the various algorithmic steps are summarized in individual 'blocks'. Such blocks describe specific actions or decisions that are made or carried out as the algorithm proceeds. Where a microcontroller (or equivalent) is employed, the flow diagram presented herein provides the basis for a 'control program' that may be used by such a microcontroller (or equivalent) to effectuate the desired control of the stimulation device. Those skilled in the art may readily write such a control program based on the flow diagram and other descriptions presented herein.

Referring to FIG. 4, at step 402, a patient's heart is paced using a pacing sequence that includes at least two different types of pacing pulses. In specific embodiments, this can include pacing the patient's heart using a pacing sequence that includes both monophasic and biphasic pacing pulses. The different types of pacing pulses used in the pacing sequence alter ionic current contributions to action potentials. It is believed that a healthy heart will compensate for the changes in pacing pulses, and thus, action potential responses to different types of pacing pulses will be generally similar. In contrast, an unhealthy heart (e.g., due to heart failure and/or ischemia) with impaired cellular electrical functions (e.g., elevated extracellular potassium concentration in ischemic zone; down-regulated repolarizing potassium currents in failing heart) will not be able to compensate for changes in the pacing pulses, and thus, action potential responses to the different types of pacing pulses will differ (more than would be the case in a healthy heart). Such changes in action potential responses are observable as beat to beat alternans in an IEGM or ECG. A degree of such alternans is believed to be indicative of the health of the heart, including the electrical stability of the heart.

Step 402 can include pacing the patient's heart using a pacing sequence that includes alternating monophasic and biphasic pacing pulses, as described below with reference to FIG. 5A. Alternatively, step 402 can include pacing the patient's heart using a pacing sequence that includes a plurality of monophasic pacing pulses followed by a plurality of biphasic pacing pulses, which may repeat for a period of time. For example, the pacing sequence can include 10 monophasic pacing pulse, followed by 10 biphasic pacing pulses, followed by 10 monophasic pacing pulse, followed by 10 biphasic pacing pulses, etc., for a programmed period of time.

In still other embodiments, step 402 can include pacing the patient's heart using a pacing sequence that includes two different types of biphasic pacing pulses (i.e., at least a first type of biphasic pacing pulse and a second type of biphasic pacing pulse). For example, this can include pacing the patient's heart using a pacing sequence that includes alternating first and second types of biphasic pacing pulses. Alternatively, the pacing sequence that include a plurality of the first type of biphasic pacing pulses followed by a plurality of the second type of biphasic pacing pulses, which may repeat for a period of time.

In embodiments where the pacing sequence includes at least two difference types of biphasic pacing pulses, at least one parameter is different in the first type of biphasic pacing pulse compared to the second type of biphasic pacing pulse. Such parameters (which can be different in the first type of biphasic pacing pulses, compared to the second type of biphasic pacing pulses) include an amplitude of the first phase, an amplitude of the second phase, a pulse duration of the first phase, a pulse duration of the second phase, a polarity of the first phase, a polarity of the second phase, and a length of the coupling interval. Preferably, the difference(s) between the different types of biphasic pacing pulses are sufficient to invoke electrical alternans in an unhealthy heart.

While the above embodiments that include the use of biphasic pacing pulses are the preferred embodiments, in still other embodiments step 402 can include pacing the patient's heart using a pacing sequence that includes two different types of monophasic pacing pulses (i.e., at least a first type of monophasic pacing pulse and a second type of monophasic pacing pulse). In such embodiments, at least one parameter is different in the first type of monophasic pacing pulse as compared to the second types of monophasic pacing pulse. Such parameters (which can be different in the first type of monophasic pacing pulses, as compared to the second type of biphasic pacing pulses) include a pulse amplitude, polarity, pulse duration, and pulse shape. Preferably, the difference(s) between the different types of monophasic pacing pulses are sufficient to invoke electrical alternans in an unhealthy heart. In still other embodiments, step 402 can include the use of triphasic pacing pulses. For example, a patient's heart can be paced using two different types of triphasic pacing pulses, or triphasic and biphasic pacing pulses, or triphasic and monophasic pacing pulses. However, it is noted that triphasic pacing pulses are typically not used as often as monophasic and biphasic pacing pulses due to the increased hardware complexity necessary to produce triphasic pulses. Nevertheless, use of triphasic pacing pulses are also within the scope of the present invention.

As explained above, it is undesirable to significantly elevate the heart rate of certain patient populations. Accordingly, in preferred embodiments of the present invention, the pacing sequences described above are delivered at a rate that is only slightly greater than the patients intrinsic rate, and more specifically, preferably at a rate that is only high enough to ensure capture in response to the pacing (as opposed to capture in response to intrinsic electrical activity). For example, in specific embodiments, the pacing rate, at which the patient's heart is paced at step 402, is greater than the patient's intrinsic heart rate but within approximately 20% of the patient's intrinsic heart rate, and preferably within 10% of the intrinsic rate.

The pacing sequence delivered at step 402 should be delivered for a long enough period that the patient's heart has a time to sufficiently respond to the pacing sequence. In specific embodiments, the pacing sequence is delivered for at least 30 seconds, at step 402. However, delivery of the pacing sequence for more or less than 30 second is also within the scope of the present invention. In specific embodiments, the pacing sequence is delivered for about 2 minutes. Exemplary leads and electrodes that can be used to deliver the pacing sequences were discussed above with reference to FIGS. 1 and 2. However, embodiments of the present invention should not be limited to using those exemplary leads and electrodes.

Referring again to FIG. 4, at step 404, there is a determination of a degree of alternans in a signal (e.g., an ECG or IEGM) that is indicative of cardiac activity in response to the pacing sequence. An electrocardiogram (ECG) can be obtained from non-implanted electrodes, e.g., placed on a patient's chest, or implanted subcutaneous electrodes. An intracardiac electrogram (IEGM) can be obtained, e.g., using leads placed within or in close proximity to the patient's heart. Exemplary leads 20, 24 and 30 were discussed above with reference to FIG. 1, and exemplary electrodes connected to such leads were discussed above with reference to FIGS. 1 and 2. However, other leads and/or electrodes can alternatively be used to obtain the signal that is indicative of cardiac activity in response to the pacing sequence.

In accordance with specific embodiments, step 404 includes comparing portions of an ECG or IEGM that are indicative of cardiac activity in response to the first type of pacing pulses to portions of the signal that are indicative of cardiac activity in response to the second type of pacing pulses, in order to determine the degree of alternans. For example, where the first type of pacing pulses are monophasic pacing pulses, and the second type of pacing pulses are biphasic pacing pulses, step 404 can involve comparing portions of an ECG or IEGM that are indicative of cardiac activity in response to monophasic pacing pulses to portions of the ECG or IEGM that are indicative of cardiac activity in response to biphasic pacing pulses, in order to determine a degree of alternans. In other embodiments, where a pacing sequence includes two different types of biphasic pacing pulses, step 404 can include comparing portions of an ECG or IEGM that are indicative of cardiac activity in response to the first type of biphasic pulses to portions of the ECG or IEGM that are indicative of cardiac activity in response to the second type of biphasic pacing pulses, in order to determine the degree of alternans.

Step 404 can include measuring at least one metric of the morphology of cardiac cycles, and determining the degree of alternans based on the measured metrics. For example, this can include measuring at least one metric of T-waves, and determining the degree of alternans based on the measured T-wave metrics. Exemplary metrics of T-waves that can be measured include, but are not limited to T-wave amplitude, T-wave width, T-wave slope, T-wave area, T-wave morphology, QT interval, and evoked QT interval. While it is expected that alternans will be revealed to a greatest extent within the T-waves, that is not always the case. Accordingly, it is also within the scope of the present invention to analyze for alternans in other portions of a cardiac cycle, such as the P-wave, or R-wave, but not limited thereto. Exemplary details of how degrees of alternans can be determined are provided below.

Figure 5A:
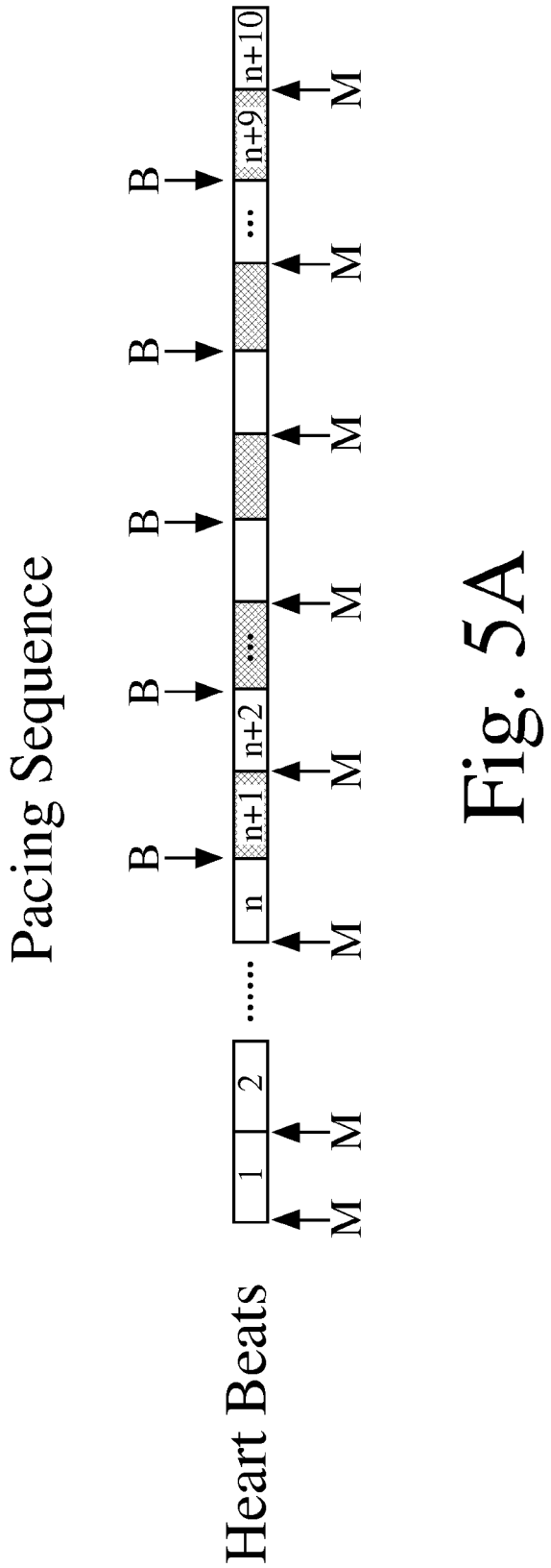
FIG. 5A is a schematic representation of a pacing sequence, of an embodiment of the present invention, used in a computer simulation.
Figure 5B:
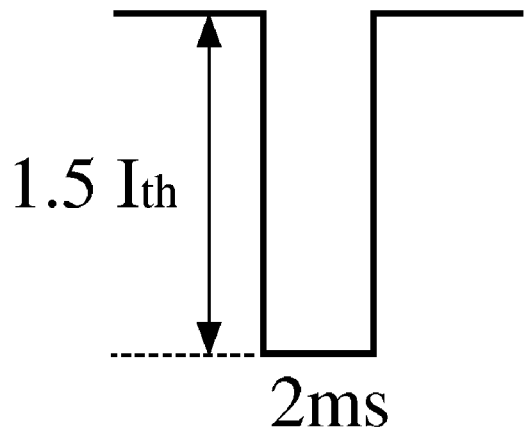
FIG. 5B includes a schematic representation of a monophasic pacing pulse and a biphasic pacing pulse, used in the computer simulated pacing sequence of FIG. 5A.
Figure 5B:
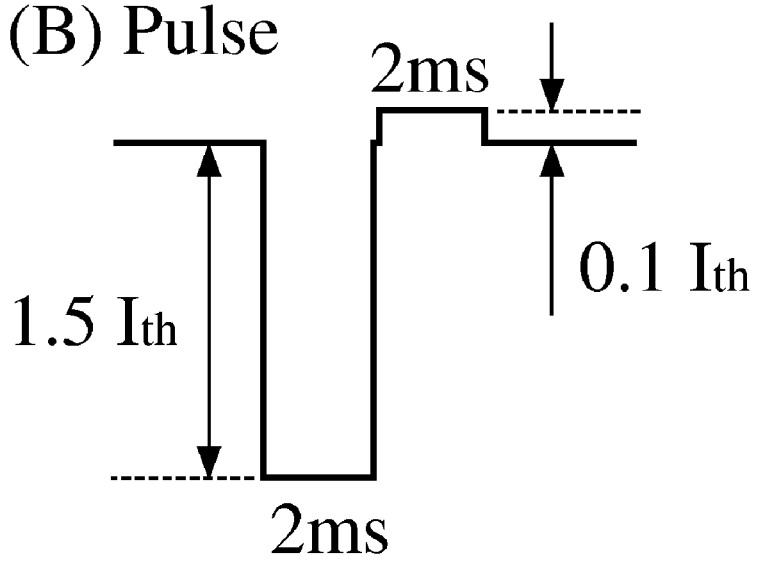

For the following explanation, it is assumed that the pacing sequence used includes alternating monophasic and biphasic pacing pulses, e.g., as shown in FIG. 5B discussed below. In other words, it will be assumed that odd beats of a pacing sequence are monophasic, and even beats of the pacing sequence are biphasic. It can also be assumed that a T-wave metric is being measured to determine the degree of alternans. One way to measure a degree of alternans is to measure T-wave metrics for all beats represented in an ECG or IEGM that occur in response to a pacing sequence, and then line up all the T-wave metrics of odd beats, and line up all the T-wave metrics of even beats. Ensemble averaging (or some other averaging) can then be performed to produce one or more average "odd" T-wave metric and one or more average "even" T-wave metric. A degree of alternans can then be determined by determining a difference between an average "odd" T-wave metric and a corresponding average "even" T-wave metric.

It is evident that the algorithm used to assess a degree of alternans should appropriately correspond to the type of pacing sequence used. For example, assume that a pacing sequence includes 10 monophasic pacing pulses followed by 10 biphasic pacing pulses, which is repeated for two minutes. To determine a degree of alternans, T-wave metrics in response to the monophasic pacing pulses should be compared to T-wave metrics in response to biphasic pacing pulses. This can be accomplished, e.g., by averaging (or adding) T-wave metrics of beats that occurred in response monophasic pacing pulses, and averaging (or adding) T-wave metrics of beats that occurred in response to biphasic pacing pulses, and then determining a difference between the two averages (or two sums). This can alternatively be accomplished by comparing T-wave metrics of the beats that occurred in response to the last (e.g., 10th), or last few, biphasic pacing pulses to T-wave metrics of the beats that occurred in response to the last (e.g., 10th), or last few, monophasic pacing pulses of the pacing sequence. Such an embodiment would enable action potentials to reach a steady state, in response to the changed pacing pulses. In still other embodiments, this can be accomplished by comparing T-wave metrics of the beats that occurred in response to the last (e.g., 10th), or last few, biphasic pacing pulses to T-wave metrics of the beats that occurred in response to the first, or first few, monophasic pacing pulses of the pacing sequence. In a further embodiments, this can be accomplished by comparing T-wave metrics of the beats that occurred in response to the last (e.g., 10th), or last few, monophasic pacing pulses to T-wave metrics of the beats that occurred in response to the first, or first few, biphasic pacing pulses of the pacing sequence. One of ordinary skill in the art would appreciate from this discussion that there are almost indefinite variations on such algorithms, and that any know electrical alternans (including Twave alternans) detection techniques can be tailored to be used with embodiments of the present invention. For example, frequency domain analysis can be used for determining degrees of alternans.

Exemplary systems and methods for detecting electrical alternans, and more generally, monitoring myocardial electrical stability, are provided in the following commonly assigned applications, which are both incorporated herein by reference: U.S. patent application Ser. No. 11/354,699, entitled "Time Domain Monitoring of Myocardial Electrical Stability,", and U.S. Patent Application No. 11/354,732, entitled "Frequency Domain Monitoring of Myocardial Electrical Stability,", both of which were filed Feb. 14, 2006. The techniques used in these applications can be used or tailored to be used to detect degrees of alternans in response to the pacing sequences of embodiments of the present invention.

These are just a few examples of the ways in which degrees of alternans can be detected, or more generally, that myocardial electrical stability can be monitored, at step 406. One of ordinary skill in the art will appreciate that many other different techniques can be used, while still being within the spirit and scope of the present invention. One of ordinary skill in the art will also appreciate that alternative metrics of beat morphology, besides T-wave metrics, can reveal alternans, as mentioned above.

Still referring to FIG. 4, at step 406, the patient's myocardial electrical stability is assessed based on the determined degree of alternans. Step 406 can include assessing a patient's risk of an adverse cardiac event, such as a tachyarrhythmia and/or sudden cardiac death (SCD). Step 406 can include comparing the degree of alternans, determined at step 404, to one or more threshold. The determination of the patient's myocardial electrical stability can then be based on a result of the comparison. For example, if the difference is less than a threshold, then it can be determined that the patient's myocardial electrical stability is good, and thus, that the patient is not at risk of a tachyarrhythmia and/or SCD. If the degree of alternans is greater than a specific threshold, then it can be determined that that patients myocardial electrical stability is poor, and that the patient may be at risk of a tachyarrhythmia and/or SCD. This can also be used for tracking the progression of a disease that influences the electrical stability of the myocardium. Additionally, a degree of the T-wave alternans (or more generally, a degree of alternans) can be used as an index of the level of risk for an impending adverse cardiac event. In such embodiments, an alert and/or response can be triggered if there is an assessment that the patient is at risk of an adverse cardiac event, as indicated at step 408.

Stated another way, in specific embodiments, the induced beat to beat variations in an ECG or IEGM are used as a risk indicator of tachyarrhythmia and sudden cardiac death. It is believed that the pacing sequences of the present invention will induce small alterations in the healthy heart, but create relatively large alterations in the diseased heart. Additionally, or alternatively, embodiments of the present invention can be used as a tool to detect and track the progress of heart diseases. The rationale for such embodiments is that the changes of amplitude and morphology in an ECG and IEGM will be tightly associated with the degree of heart diseases.

Steps 402, 404, 406 and 408 can all be performed autonomously by an implanted system (e.g., ICD 10) that is adapted to pace a patient's heart. Alternatively, all, or some, of the steps can be performed by or under the control of a non-implanted system (e.g., external device 102), which wirelessly communicates with an implanted system (e.g., ICD 10) adapted to pace the patient's heart.

If is determined at step 406 that the degree of alternans is indicative of the patient having a heightened risk of an arrhythmic events (such as a tachyarrhythmia, and more specifically a ventricular arrhythmia), then arrhythmia prevention therapy can be triggered at step 408. One type of therapy would be for an implanted device (e.g., device 10) to stimulate the patient's vagus nerve, in an attempt to prevent an arrhythmia from occurring. In another embodiment, the implanted device, if appropriately equipped, can deliver appropriate anti-arrhythmia drug therapy. In still another embodiment, the implanted device, if appropriately equipped, can deliver appropriate pacing therapy, including, but not limited to, resynchronization therapy. In still another embodiment, the implantable device, if capable of delivering shock therapy, can begin to charge its capacitors in case the patient goes into ventricular fibrillation and needs shock therapy. These are just a few examples of the types of responses that can be performed upon detection of a heightened risk of an arrhythmia. One of ordinary skill in the art would understand from the above description that other responses are also possible, while still being within the spirit and scope of the present invention.

If is determined at step 406 that the degree of alternans is indicative of the patient having a heightened risk of an acute heart failure exacerbation, then at step 408 an appropriate therapy can be triggered. One type of therapy would be for an implanted device, if appropriately equipped, to deliver appropriate drug therapy. In another embodiment, the implantable device can perform appropriate pacing therapy to treat an acute heart failure exacerbation. One of ordinary skill in the art would understand from the above description that other responses are also possible, while still being within the spirit and scope of the present invention.

Additionally or alternatively, a patient can be alerted (e.g., using alert 118) at step 408 if e.g., at step 406 there is a detection of a heightened risk of an arrhythmia, SCD and/or an acute heart failure exacerbation. The same alert can be used for each type of detected heightened risk, or the alert can be specific to the type of risk. For example, a first type of alert can be triggered if it is determined that the patient is at a heightened risk of an arrhythmia and a second type of alert (distinguishable from the first type of alert) can be triggered if it is determined that the patient is at a heightened risk of an acute heart failure exacerbation.

An alert could be a vibratory or auditory alert that originates from within the implantable device 10. Alternatively, the implantable device 10 may wirelessly transmit an alert to an external device (e.g., 102) that produces a visual or auditory alert that a patient can see or hear. The alert may inform that patient that he should rest, or if the patient is operating some type of dangerous machinery (e.g., a car), that the patient should stop what they are doing. By alerting the patient to rest, it is possible an arrhythmia may be avoided, or if it does occur, the patient will be less dangerous to themselves and others if the patient is resting when the arrhythmia occurs (as opposed, e.g., to driving a car). It is also possible that the alert can be generated by an external device (e.g., 102).

Additionally or alternatively, the patient can be instructed to take medication when alerted. Additionally or alternatively, a caregiver (e.g., physician) can be alerted if it is determined that the patient is at a heightened risk of an arrhythmia, SCD and/or an acute heart failure exacerbation. Additionally or alternatively, information related to the degree of alternans can be stored. This can include, for example, storing amplitude, slope, timing, and/or duration information relating to the alternans. If such information is stored in an implanted device, such information can be continually, or from time to time, automatically uploaded to an external device (e.g., 102). Such an external device 102 can be located, e.g., in the patient's home, and the information can be transmitted (e.g., through telephone lines or the Internet) to a medical facility where a physician can analyze the information. For example, the external device 102 can be a bedside monitor, or an ambulatory device that the patient carries with them. Alternatively, the external device 102 can be an external programmer located at a medical facility, and the information can be uploaded when the patient visits the facility.

One or more of the above described responses can be triggered if the electrical instability of the myocardium exceeds a corresponding threshold, or electrical stability of the myocardium falls below a corresponding threshold.

In a specific embodiment, degrees of alternans are tracked over time to thereby track how a patient's myocardial electrical stability (and/or risk of a tachyarrhythmia and/or risk of SCD) changes over time. For example, a same pacing sequence intended to invoke alternans in an unhealthy heart can be delivered once per day (or week, or month or other period), and a degree of alternans can be determined each time. More specifically, steps 402, 404 and 406 can be repeated over time, to thereby track changes in the patient's myocardial electrical stability, risk of tachyarrhythmia and/or risk of SCD. This can enable the monitoring of changes in a cardiac disease, such as ischemia and or heart failure. More specifically, steps 402 and 404 can be repeated over time, wherein each time steps 402 and 404 are performed, an updated degree of alternans is determined. Changes in the cardiac disease can then be monitored based on changes in determined degree of alternans. For example, a reduction in the degree of alternans can be interpreted as being indicative of an improvement in the cardiac disease, an improvement in myocardial electrical stability, a reduction in a risk of a tachyarrhythmia and/or a reduction in a risk of SCD. In contrast, an increase in the degree of alternans can be interpreted as being indicative of a worsening of the cardiac disease, a worsening in myocardial electrical stability, an increase in a risk of a tachyarrhythmia and/or in increase in a risk of SCD.

Figure 5C:
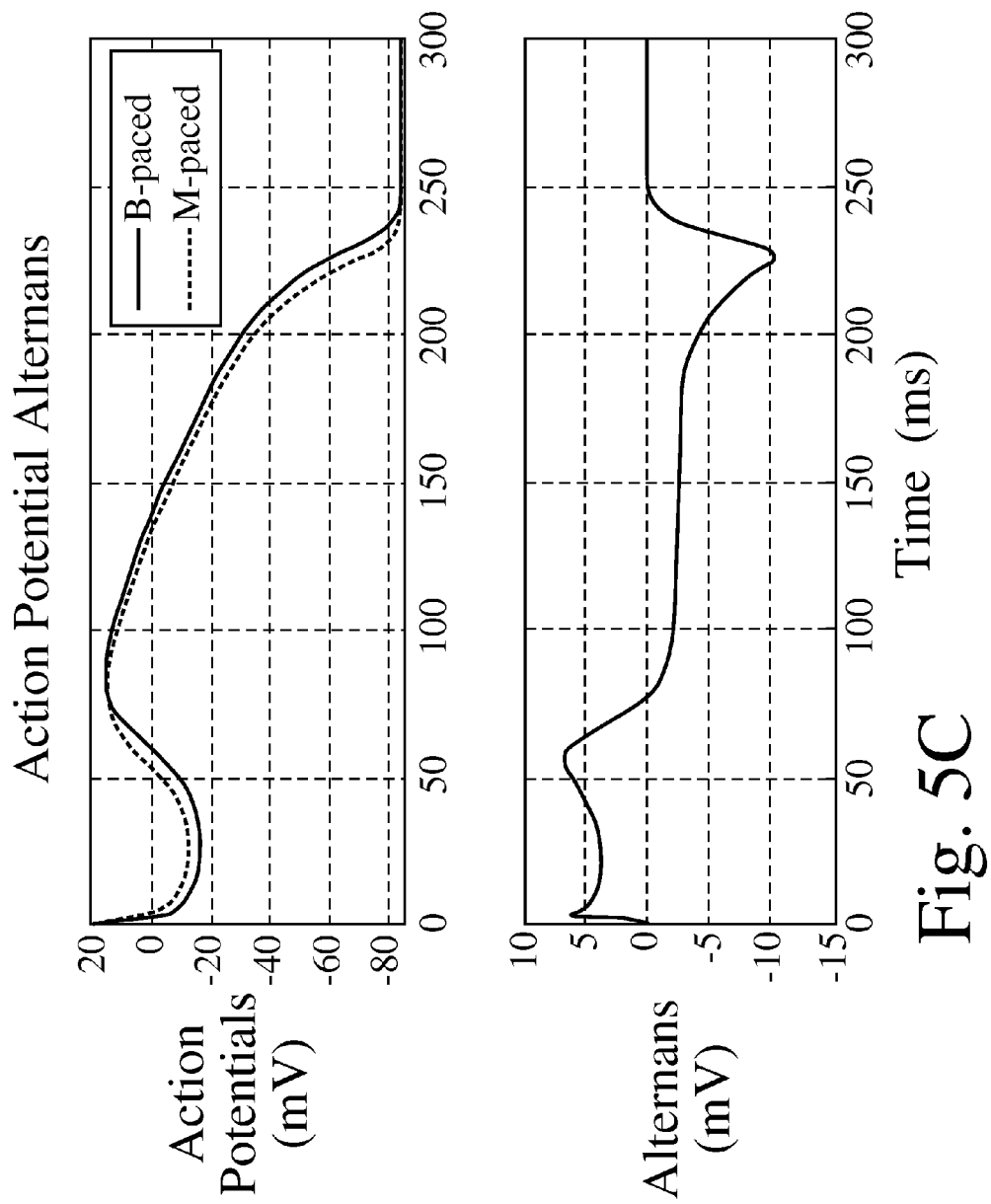
FIG. 5C includes an upper plot that shows computer simulated cardiac ventricular action potential responses to biphasic pacing pulses (solid line) and monophasic pacing pulses (dashed line), and a lower plot that shows action potential alternans determined by subtracting the action potential response to the biphasic pacing pulses from the action potential response to the monophasic pacing pulses.

Information regarding degrees of alternans can be saved in an implanted device (e.g., 10) and uploaded to a non-implanted device (e.g., 102) from time to time, or otherwise obtained by the non-implanted device, so that trends in cardiac disease and/or myocardial electrical stability can be displayed to a physician. For example, a line or bar graph of degrees of alternans versus time can be produced and displayed based on such information. Additionally, or alternatively, a histogram can be produced and displayed. Each bin of the histogram can represent, e.g., the number of times or length of time during each period (e.g., week) that a degree of alternans threshold was crossed. Numerous other ways for displaying such information are also possible, and within the scope of the present invention. The non-implanted device can also store such information, so that the displayed graphs and/or histograms can be updated each time updated information is provided to the non-implanted device Computer Simulations To investigate the validity of techniques of the present invention, computer models of healthy and diseased myocardial cells were constructed. The model of a healthy myocardial cell was treated as being indicative of a healthy heart. The model of unhealthy myocardial cells were treated as being indicative of unhealthy hearts. FIG. 5A illustrates the pacing sequence that was used in the computer simulations to attempt to induce action potential alternans at a normal pacing rate, e.g., of about 70 bpm. As can be seen in FIG. 5A, the simulated pacing sequence alternated continuously between a monophasic pulse (M-pulse) and a biphasic pulse (B-pulse). Schematic representations of the monophasic and biphasic pacing pulses used in the computer simulation are shown in FIG. 5B. In the computer simulations, the action potential alternans were computed by subtracting a previous action potential from a current action potential. The upper plot of FIG. 5C illustrates the simulated action potential response to monophasic pulses (dashed line) and a simulated action potential response to biphasic pulses (solid line). The lower plot in FIG. 5C illustrates the simulated action potential response to the biphasic pulses subtracted from the simulated action potential response to the monophasic pulses. Exemplary details of how myocardial cells can be modeled are provided in the following articles, each of which are incorporated herein by reference: Hund et al "Rate Dependence and Regulation of Action Potential and Calcium Transient in a Canine Cardiac Ventricular Cell Model," Circ. 2004 Nov. 16; 110(20):3168-74; and Priebe et al. "Simulation Study of Cellular Electric Properties in Heart Failure," Circ Res. 1998 Jun. 15; 82(11):1206-23.

Figure 6A:
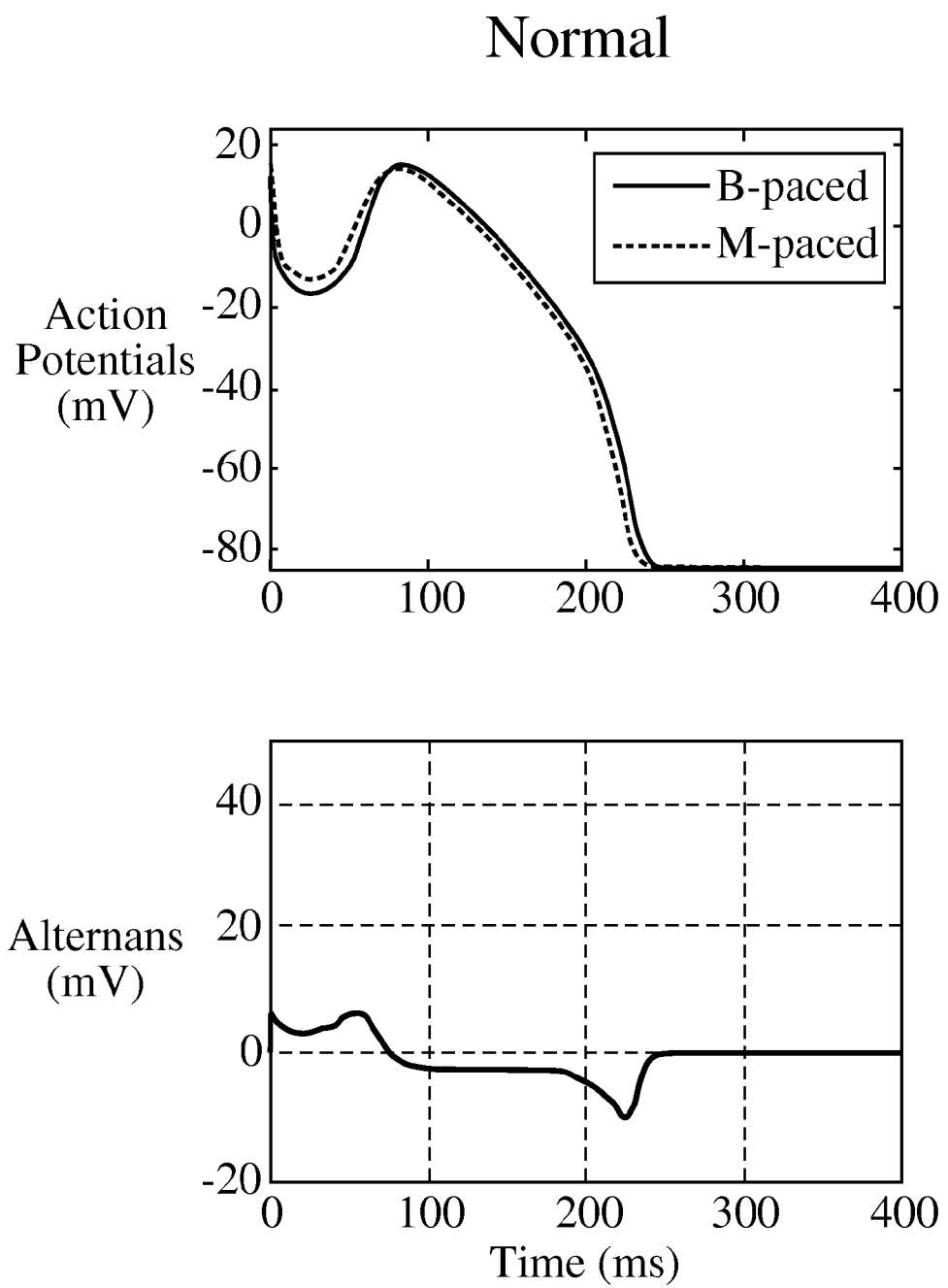
FIG. 6A includes an upper plot that shows computer simulated cardiac ventricular action potential responses for a normal (i.e., healthy) heart to biphasic pacing pulses (solid line) and monophasic pacing pulses (dashed line), and a lower plot that shows action potential alternans determined by subtracting the action potential response to the biphasic pacing pulses from the action potential response to the monophasic pacing pulses.

The plots of FIG. 5C, which are substantially the same as the plots of FIG. 6A, show that a degree of alternans for a healthy myocardial cell is relatively low. More specifically, it can be seen in the upper plots of FIGS. 5C and 6A that action potential responses to biphasic and monophasic pacing pulses for a healthy myocardial cell are almost the same. This results in the amplitude and area under the curve (indicative of the difference between the curves) of the lower plot being relatively small.

Figure 6B:
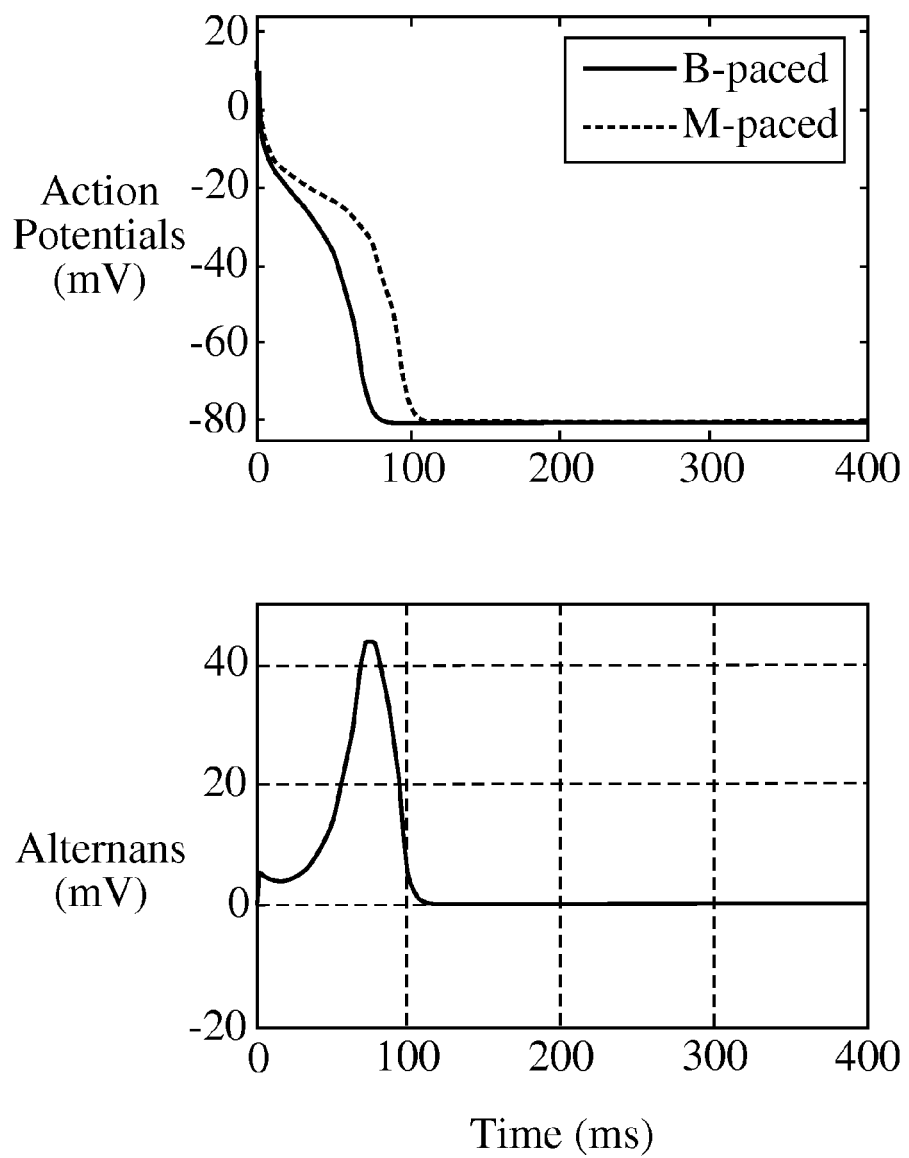
FIG. 6B includes an upper plot that shows computer simulated cardiac ventricular action potential responses for an ischemic heart to biphasic pacing pulses (solid line) and monophasic pacing pulses (dashed line), and a lower plot that shows action potential alternans determined by subtracting the action potential response to the biphasic pacing pulses from the action potential response to the monophasic pacing pulses.
Figure 6C:
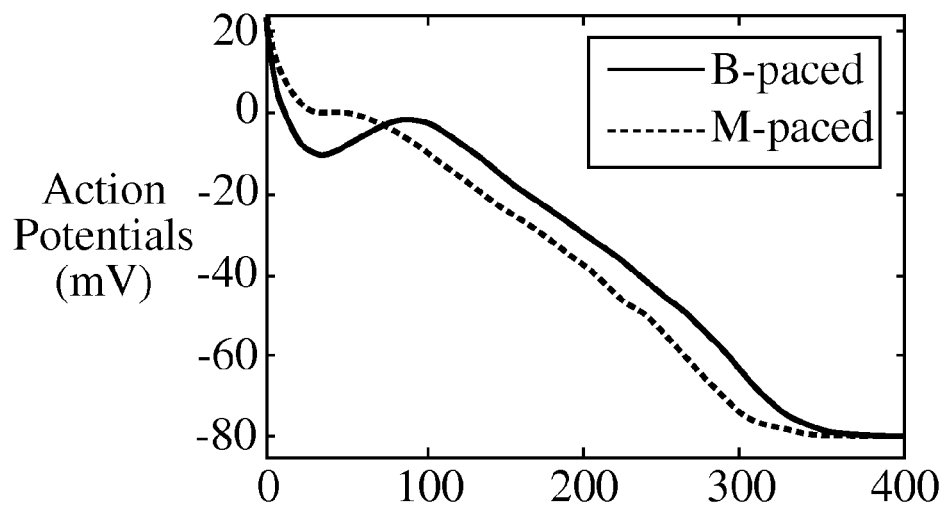
FIG. 6C includes an upper plot that shows computer simulated cardiac ventricular action potential responses for a heart having heart failure to biphasic pacing pulses (solid line) and monophasic pacing pulses (dashed line), and a lower plot that shows action potential alternans determined by subtracting the action potential response to the biphasic pacing pulses from the action potential response to the monophasic pacing pulses.
Figure 6C:
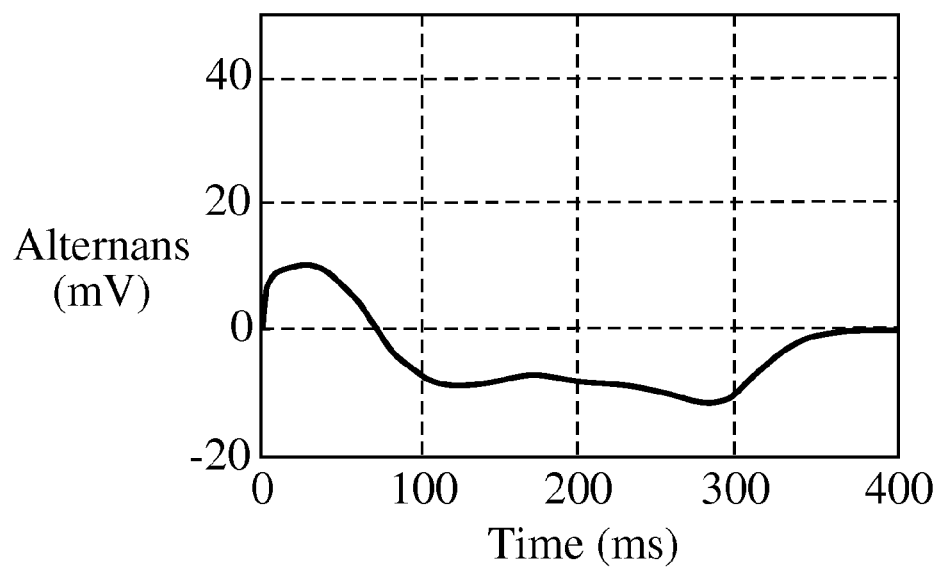
Figure 6D:
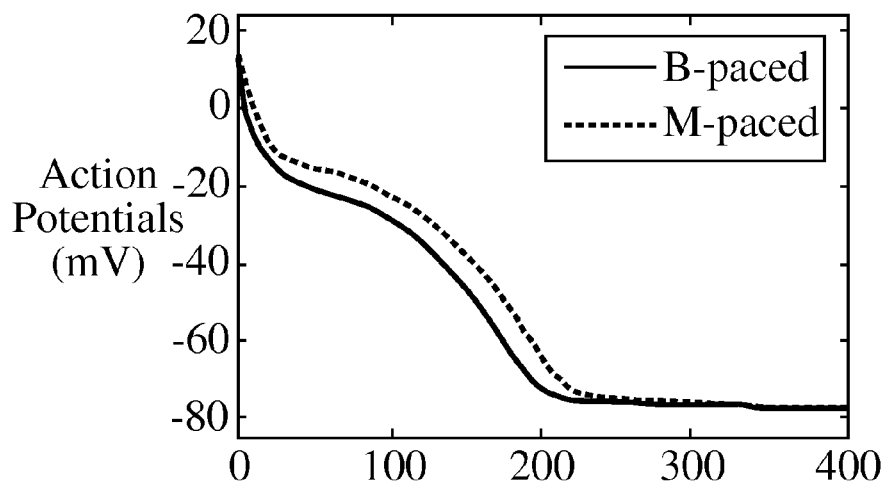
FIG. 6D includes an upper plot that shows computer simulated cardiac ventricular action potential responses for a heart having ischemia and heart failure to biphasic pacing pulses (solid line) and monophasic pacing pulses (dashed line), and a lower plot that shows action potential alternans determined by subtracting the action potential response to the biphasic pacing pulses from the action potential response to the monophasic pacing pulses.
Figure 6D:
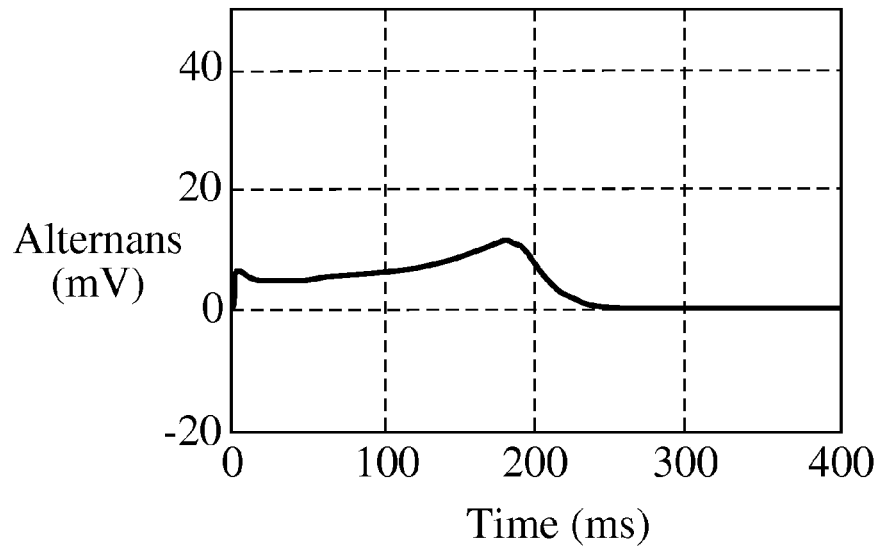

FIGS. 6B, 6C and 6D, show simulated results when the pacing sequence of FIG. 5A was applied, respectively, to a myocardial cell that is ischemic (FIG. 6B), has heart failure (FIG. 6C), and has ischemia and heart failure (FIG. 6D). As can be appreciated from these figures, the action potential responses to biphasic and monophasic pacing pulses (shown in the upper plots) are different for unhealthy myocardial cells. This results in the amplitude and area under the curves of the lower plots being significantly larger than shown in the lower plot of FIGS. 5C and 6A. For each of these simulations, the overall pacing rate used in the simulation model was only slightly above (i.e., within 10% of) a normal resting heart rate of 70 beats per minute (bpm).

Also simulated, but not shown, was the delivery of standard pacing pulses (i.e., identical monophasic pacing pulses) to each of the myocardial cells modeled and discussed in FIGS. 6A-6D. The action potential responses to standard pacing pulses, at slightly above the intrinsic rate, were substantially the same whether the cell was healthy or diseased.

In summary, when pacing at a rate only slightly above an intrinsic rate, action potentials of a healthy heart remain relatively unchanged in response to standard pacing as well in response to a pacing sequence of alternating monophasic and biphasic pacing pulses. However, for an unhealthy heart, while standard pacing at a rate only slightly above an intrinsic rate will not cause alternans, pacing at the rate only slightly above the intrinsic rate will cause alternans when the pacing using an alternating monophasic and biphasic pacing sequence of an embodiment of the present invention.

The action potential alternans induced in myocardial cells (as explained with reference to FIGS. 6A-6D) are observable in an ECG and IEGM, and the changes in the amplitude and morphology of ECG and IEGM is associated with different heart diseases and their corresponding degree. Accordingly, embodiments of the present invention can be implemented into ICD device routines in order to predict the progress of heart diseases and associated degree of vulnerability to ventricular arrhythmias, ischemia and SCD. Embodiments of the present invention can also be implemented using external devices, such as external programmer that can control an implanted cardiac device.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

Example embodiments of the methods, systems, and components of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed:

1. A method for assessing a patient's myocardial electrical stability, comprising:
   (a) obtaining a signal that is indicative of cardiac activity in response to pacing a patient's heart using a pacing sequence that includes both monophasic and biphasic pacing pulses;
   (b) comparing portions of the signal that are indicative of cardiac activity in response to monophasic pacing pulses to portions of the signal that are indicative of cardiac activity in response to biphasic pacing pulses to thereby determine a degree of alternans in the signal that is indicative of cardiac activity in response to the pacing sequence; and
   (c) assessing the patient's myocardial electrical stability based on the determined degree of alternans.

2. The method of claim 1, wherein step (a) comprises pacing the patient's heart using a pacing sequence that includes alternating monophasic and biphasic pacing pulses.

3. The method of claim 1, wherein step (a) comprises pacing the patient's heart using a pacing sequence that includes a plurality of monophasic pacing pulses followed by a plurality of biphasic pacing pulses.

4. The method of claim 1, wherein a pacing rate, at which the patient's heart is paced at step (a), is greater than the patient's intrinsic heart rate but within approximately 10% of the patient's intrinsic heart rate.

5. The method of claim 1, wherein the pacing of the patient's heart using the pacing sequence at step (a) is for at least 30 seconds.

6. The method of claim 1, wherein step (b) includes:
   (b.1) measuring at least one metric of the morphology of cardiac cycles; and
   (b.2) determining the degree of alternans based on the measured metrics.

7. The method of claim 6, wherein step (b) includes:
   (b.1) measuring at least one metric of T-waves; and
   (b.2) determining the degree of alternans based on the measured T-wave metrics.

8. The method of claim 1, wherein step (c) includes:
   (c.1) comparing the degree of alternans to at least one threshold; and
   (c.2) assessing the patient's myocardial electrical stability based on a result of the comparison performed at (c.1).

9. The method of claim 1, further comprising tracking changes in the degree of alternans as steps (a), (b) and (c) are repeated over time, to thereby track changes in the patient's myocardial electrical stability.

10. The method of claim 1, wherein steps (a), (b) and (c) are performed by an implanted system.

11. The method of claim 1, wherein steps (a), (b) and (c) are performed under the control of a non-implanted system that wirelessly communicates with an implanted system adapted to pace the patient's heart.

12. The method of claim 1, wherein step (c) includes assessing a patient's risk of a tachyarrhythmia.

13. The method of claim 12, further comprising:
   (d) triggering an alert and/or response if there is an assessment at step (c) that the patient is at risk of a tachyarrhythmia.

14. The method of claim 1, wherein step (c) includes assessing a patient's risk of sudden cardiac death (SCD).

15. A method for monitoring a cardiac disease, comprising:
   (a) obtaining a signal that is indicative of cardiac activity in response to pacing a patient's heart using a pacing sequence that includes both monophasic and biphasic pacing pulses;
   (b) comparing portions of the signal that are indicative of cardiac activity in response to monophasic pacing pulses to portions of the signal that are indicative of cardiac activity in response to biphasic pacing pulses to thereby determine a degree of alternans in the signal that is indicative of cardiac activity in response to the pacing sequence;
   (c) repeating steps (a) and (b) over time, wherein each time steps (a) and (b) are performed an updated degree of alternans is determined; and
   (d) monitoring changes in the cardiac disease based on changes in determined degree of alternans.

16. The method of claim 15, wherein the cardiac disease that is being monitored is at least one of ischemia and heart failure.

17. The method of claim 15, wherein (d) includes:
   interpreting a reduction in the degree of alternans as being indicative of an improvement in the cardiac disease; and
   interpreting an increase in the degree of alternans as being indicative of a worsening of the cardiac disease.

18. The method of claim 15, wherein step (a) comprises pacing the patient's heart using a pacing sequence that includes alternating monophasic and biphasic pacing pulses.

19. The method of claim 15, wherein step (a) comprises pacing the patient's heart using a pacing sequence that includes a plurality of monophasic pacing pulses followed by a plurality of biphasic pacing pulses.

20. A system for assessing a patient's myocardial electrical stability, comprising:
   one or more pulse generator to produce a pacing sequence that includes both monophasic and biphasic pacing pulses;
   one or more sensing circuit to obtain a signal that is indicative of cardiac activity in response to pacing using the pacing sequence that includes both monophasic and biphasic pacing pulses;
   an alternans detector to compare portions of the signal that are indicative of cardiac activity in response to monophasic pacing pulses to portions of the signal that are indicative of cardiac activity in response to biphasic pacing pulses to thereby determine a degree of alternans in the signal that is indicative of cardiac activity in response to the pacing sequence; and
   a stability detector to assess a patient's myocardial electrical stability based on the determined degree of alternans.

21. The system of claim 20, wherein the stability detector compares the determined degree of alternans to one or more threshold to assess a patient's myocardial electrical stability.

22. The system of claim 20, wherein the pacing sequence includes alternating monophasic and biphasic pacing pulses.

23. The system of claim 20, wherein the pacing sequence that includes a plurality of monophasic pacing pulses followed by a plurality of biphasic pacing pulses.

* * * * *